US007018658B2

(12) United States Patent
Platteeuw

(10) Patent No.: US 7,018,658 B2
(45) Date of Patent: Mar. 28, 2006

(54) PHARMACEUTICAL PELLETS COMPRISING TAMSULOSIN

(75) Inventor: Johannes J. Platteeuw, Nijmegen (NL)

(73) Assignee: Synthon BV, Nijmegen (NL)

( * ) Notice: Subject to any disclaimer, the term of this patent is extended or adjusted under 35 U.S.C. 154(b) by 380 days.

(21) Appl. No.: 10/293,940

(22) Filed: Nov. 14, 2002

(65) Prior Publication Data

US 2004/0096502 A1 May 20, 2004

(51) Int. Cl.
  *A61K 9/16* (2006.01)

(52) U.S. Cl. ........................ 424/497; 424/490
(58) Field of Classification Search ............... 424/497, 424/489, 400
  See application file for complete search history.

(56) References Cited

U.S. PATENT DOCUMENTS

| | | | |
|---|---|---|---|
| 4,731,478 A | | 3/1988 | Niigata et al. |
| 4,772,475 A | * | 9/1988 | Fukui et al. ................. 424/468 |
| 4,966,768 A | | 10/1990 | Michelucci et al. |
| 6,177,430 B1 | * | 1/2001 | Thompson et al. ..... 514/252.17 |
| 6,287,599 B1 | | 9/2001 | Burnside et al. |
| 6,368,628 B1 | | 4/2002 | Seth |
| 6,475,493 B1 | * | 11/2002 | Mulye ......................... 424/400 |

FOREIGN PATENT DOCUMENTS

| | | |
|---|---|---|
| EP | 0 034 432 B1 | 2/1981 |
| EP | 0 194 838 B1 | 9/1993 |
| EP | 0 533 297 B1 | 11/1997 |

OTHER PUBLICATIONS

NDA 20–579, FDA Office of Clinical Pharmacology and Biopharmaceutics Review, pp 1–6, 1997.
Flowmax, MIMMS Abbreviated Prescribing Information, MIMMS Australia, 1996–2002.
Presentation entitled: "*In Vivo* Performance of Hydrophilic Matrix Tablets Utilizing HPMC: Case Studies" by Tim D. Cabelka, Ph.D. and Thomas D. Reynolds, Ph.D. , The Dow Chemical Company, Oct. 17, 2000.
FDA–FOIA Labeling Information for Flomax®, 2001.
Dunn CJ, Matheson A and Faulds DM. "Tamsulosin A review of its pharmacology and therapeutic efficacy in the management of lower urinary tract symptoms." *Drugs Aging* 2002; 19; 135–161.
Dutkiewics S. "Efficacy and tolerability of drugs for treatment of benign prostatic hyperphasia." *Int Urology and Nephrology* 2001; 32; 423–432.
Harada K. and Fujimara A. "Clinical pharmacology of $_{1A}$ selective and nonselective $_1$–blockers." *BJU International* 2000; 86; 31–35.
Lyseng–Williamson KA, Jarvis B and Wagstaff AJ. "Tamsulosin An update of its role in the management of lower urinary tract symptoms." *Drugs* 2002; 62; 135–167.
Michel MC, Neumann HG, Mehlburger L, Schumacher H and Goepel M. "Does the time for administration (morning or evening) affect the tolerability or efficacy of tamsulosin ?" *BJU International* 2001; 87; 31–34.
Soeishi Y, Korobi M, Kobayashi SI and Higuchi S. " Sensitive method for the determination of amsulosin in human plasma using high–performance liquid chromatography with fluorescence detection" *J of Chromatography* 1990; 553: 291–296.
Taguchi K, Schafers RF and Michel MC. "Radioreceptor assay analysis of tamsulosin and terazosin pharmacokinetics." *Br J Clin Pharmacol* 1998; 45: 49–55.
van Hoogdalem EJ, Soeishi Y, Matsushima H and Higuchi S. "Disposition of the selective $_{1A}$ adrenoceptor antagonist tamsulosin in humans: Comparison with data from interspecies scaling." *J Pharm Sciences* 1997; 86: 1156–1161.

* cited by examiner

*Primary Examiner*—Thurman K. Page
*Assistant Examiner*—Retford Berko
(74) *Attorney, Agent, or Firm*—Mark R. Buscher

(57) ABSTRACT

Tamsulosin pellets having an advantageous release profile are formed. The pellets have an enteric coating and release less than 10% of the tamsulosin in two hours in SGF.

21 Claims, No Drawings

PHARMACEUTICAL PELLETS COMPRISING TAMSULOSIN

BACKGROUND OF THE INVENTION

The present invention relates to coated tamsulosin pellets and to unit dosage forms made therefrom.

Tamsulosin is the common name for 5-[2-[[2-(2-ethoxyphenoxy)ethyl]amino]propyl]-2-methoxy-benzenesulfonamide of the formula (1).

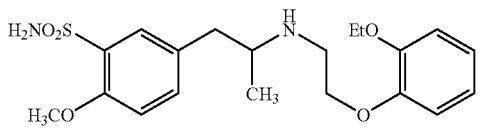

It is disclosed in EP 34432 and U.S. Pat. No. 4,731,478 as a pharmaceutically active substance having alpha-adrenergic blocking activity that is useful for treatment of cardiac insufficiencies and benign prostatic hyperplasia.

(R)-tamsulosin hydrochloride is marketed under various tradenames, including FLOMAX® (Boehringer Ingelheim) in the U.S., HARNAL® (Yamanouchi) in Japan and OMNIC® (Yamanouchi) in Europe, for treatment of symptoms of benign prostatic hyperplasia (also known as BPH) such as urinary volume and frequency problems. The approved drug products include a capsule dosage form for oral administration that comprises 0.4 mg of the tamsulosin hydrochloride. The capsule provides controlled release of the tamsulosin and is a once daily dosage form, although two capsules can be used if needed; i.e. a maximum single daily administration of 0.8 mg. U.S. Pat. No. 4,772,475 is listed in the U.S. Food and Drug Administration's *Approved Drug Products with Therapuetic Equivalence Evaluations* (the "Orange Book") as corresponding to FLOMAX®.

U.S. Pat. No. 4,772,475 (EP 194838, EP 533297) discloses controlled-release pharmaceutical dosage forms comprising multiple granulate units containing tamsulosin, microcrystalline cellulose and a release control agent. The granulate gradually releases tamsulosin from the granulate matrix. The patent suggests that an enteric coating is not needed.

The disclosed process for producing the granulate units comprises granulating a mixture of tamsulosin, an unit-forming inert material such as microcrystalline cellulose and a release controlling agent comprising water and/or an aqueous emulsion, suspension or gel of a water-insoluble macromolecular substance or a solution of said macromolecular substance in an aqueous organic solvent. The macromolecular substance is preferably selected from a range of acrylic polymers, commercially sold under brand name Eudragit®. The release controlling agent serves essentially also as a binder in the granulation process. The resulting granulate may be used for making final dosage forms, capsules as well as tablets.

Example 1 of U.S. Pat. No. 4,772,475 illustrates the process. After sufficiently mixing 5 g tamsulosin HCl and 470 g microcrystalline cellulose, a mixture of 83.3 g (25 g as solid component) of Eudragit L 30 D-55 and 500 g of water was added thereto and the resultant mixture was granulated by a high-speed mixer. The granules obtained were spheres having particle sizes of 0.1 to 1.5 mm, mainly 0.2 to 1.0 mm.

U.S. Pat. No. 4,772,475 also discloses that pellets of various compositions were prepared and tested for release characteristics according to standardized Pharmacopoeial method (paddle, 150 rpm). The reported results show that in one hour in simulated gastric fluid the release ranged from 16.2 to 60.4% of the active compound. Tablets made from some of the produced pellets, having 50.3 and 57.6% release, respectively, were also tested on human volunteers in comparison with conventional tablets and concentration of the active substance in blood plasma was measured. Peak plasma levels were reached 3 hours after ingestion (in comparison with 2 hours at conventional tablets), the total amount of tamsulosin in plasma being about 75% of that of the conventional tablet.

However, such release rate is generally not sufficiently for an extended-release dosage form. It would be desirable to provide an alternative, coated tamsulosin pellet having good release characteristics.

SUMMARY OF THE INVENTION

The present invention relates to a pharmaceutical pellet composition comprising tamsulosin as an active ingredient and having an advantageous coating layer with respect to obtaining an extended release profile. Accordingly, a first aspect of the present invention relates to a pharmaceutical dosage form comprising a plurality of pellets. Each pellet comprises a pellet core, which has a diameter within the range of 0.3–0.9 mm, comprising tamsulosin hydrochloride, microcrystalline cellulose, a pharmaceutically acceptable water permeable acrylic polymer, and water. Each pellet core is surrounded by an outer layer coat, which comprises a pharmaceutically acceptable acid-resistant acrylic polymer, in an amount, calculated on a dry pellet core basis, that is within the range of 2.5–15%. The plurality of pellets exhibits a dissolution release profile in simulated gastric fluid using Ph. Eur. basket method at 100 rpm which includes releasing less than 10% of the tamsulosin during the first two hours. Preferably the pellet core contains 2–10% water, more preferably 2.5–5% water, calculated on a dry pellet core basis, and the mass of the outer layer coat is preferably within the range of 8–12%, calculated on a dry pellet core basis.

Another aspect of the present invention relates to a process, which comprises granulating a mixture of tamsulosin hydrochloride, microcrystalline cellulose, acrylic polymer, water and optionally auxiliary ingredients to form wet pellet cores, drying the wet pellet cores to a residual amount of water of 2–10%, sieving the dried pellet cores to obtain a fraction within the size range of 0.3–0.9 mm, coating the sieved dried pellet cores with a coating composition that comprises an acid-resistant water soluble acrylic polymer, and drying the coated pellets, wherein the coating step is sufficient to provide the dried coated pellets with 2.5–15 mass % of the coating composition, calculated on the dry pellet core basis.

A further aspect of the invention relates to a process, which comprises granulating a mixture of tamsulosin hydrochloride, microcrystalline cellulose, acrylic polymer, water and optionally auxiliary ingredients to form wet pellet cores, drying the wet pellet cores to a residual amount of water of 2–10%, sieving the dried pellet cores to obtain a fraction within the size range of 0.3–0.9 mm, coating the sieved dried pellet cores with a coating composition that comprises an acid-resistant water soluble acrylic polymer, drying the coated pellets, testing a sample of the dried coated pellets for dissolution rate in a simulated gastric fluid, and repeating the coating process on the remaining dried coated pellets until a desired amount of release is achieved in the testing step. In this way, an appropriate amount of outer coat layer for a given pellet core composition, pellet core size, and outer coat layer composition can be readily determined.

DETAILED DESCRIPTION OF THE INVENTION

It has been discovered that an effective, modified release coated tamsulosin pellet composition can be formed that exhibits a dissolution release profile, when measured as a plurality of pellets, wherein less than 10% of tamsulosin is released during the first two hours in simulated gastric fluid in basket apparatus at 100 rpm, by controlling, inter alia, the amount of coating on the pellet. Accordingly, once the coated pellets of the present. invention are ingested, tamsulosin is released into the body at a rate that is characterized by minimizing the release during the pellets' residence time in the stomach environment. More advantageously, the pellet core size and composition as well as the material and amount of the coating are so selected that the resulting coated collection of pellets exhibits at least one of the following release rates in in simulated intestinal fluid (sometimes referred to herein as phosphate buffer of pH 6.8), using Ph.Eur.basket method at 100 rpm: 15–45% of the tamsulosin released in 30 minutes, 30–65% of the tamsulosin released in one hour, and more than 80% of the tamsulosin released in five hours. More preferably, the pellets satisfy all three release rates.

For clarity sake, the composition of simulated gastric fluid (SGF) and simulated intestinal fluid (SIF), although well known in the art as standard solutions, are set forth below:
SGF (USP Simulated Gastric Fluid without pepsin) composition:

| HCl | qs | pH 1.2 |
| NaCl | | 0.2% |
| water | qs | 1000 ml |

SIF (USP Simulated Intestinal Fluid without pancreatin) composition:

| $KH_2PO_4$ | | 6.8 g |
| NaOH | qs | pH 6.8 |
| water | qs | 1000 ml |

The pellets of the present invention include a pellet core having a diameter within the range of 0.3–0.9 mm, which comprises tamsulosin hydrochloride, microcrystalline cellulose, pharmaceutically acceptable water permeable acrylic polymer and water. Within the invention, an "acrylic polymer" means a pharmaceutically acceptable copolymer of methacrylic acid and an acrylic or methacrylic acid ester, such as sold under brand name Eudragit. Such compounds are, e.g., defined in Handbook of Pharmaceutical excipients, edited by A. H. Kibbe, Pharmaceutical Press London, $3^{rd}$ ed. (2000). The release of the active substance from the admixture with such acrylic polymers may or may not be dependent on the environmental pH.

In the composition of the pellet core, the microcrystalline cellulose serves as a suitable inert carrier. The acrylic polymer in the core serves as a binder and a release-controlling agent. Preferably, the polymer is an acid-resistant acrylic polymer, which releases tamsulosin dependent upon the pH. Such polymers include Eudragit L products, especially Eudragit L 30 D. Eudragit L 30 D-55 is available as a 30% (m/V) aqueous dispersion of the acrylate polymer containing also polysorbate 80 and sodium lauryl sulphate as emulsifiers.

Alternatively, two types of release control agents may be combined together in order to induce both time-dependent and pH-dependent control of the release of tamsulosin. Use of agents that release the active substance independently of environmental pH prevents a dose dumping after the pellet core surface comes into contact with the body fluid, while agents releasing the active substance pH-dependently allow to focus the release of a main portion of the active component into desired part of gastrointestinal tract. An example of the polymer that releases substances independently of the pH is hydroxypropyl methylcellulose.

The pellet core typically contains 0.05–5.0% mass of tamsulosin hydrochloride, 50–95% mass of microcrystalline cellulose, 2.5–25%, preferably 2.5–10%, more preferably 5%, mass of the acrylic polymer, 2–10%, preferably 2.5–5%, mass of water, and 0–25%, preferably 0.5–25%, mass of other pharmaceutically acceptable excipients, calculated on the total mass of the dried core. As used herein the "dried core" means a core that has been substantially dried and has a residual solvent content from the production thereof of 15% or less, more preferably 10% or less. Water is the most suitable solvent in the process of pellet formation, however it is almost completely removed afterwards. It is nevertheless important that water is present in the dried composition of the core as it affects, sometimes significantly, the rate of diffusion once the coating has been dissolved in the intestinal fluid. Hence, the pellet core requires the above amount of water to remain in the dried cores.

The "other" pharmaceutically acceptably excipients, if present, are generally used to provide proper characteristics of the composition within the pelletization procedure and include, inter alia, plasticizers (e.g. triethylcitrate) or an anti-sticking agent (e.g. talc).

Additionally, the pellets of the present invention comprise an outer layer coat surrounding the pellet core, which comprises a pharmaceutically acceptable acid-resistant acrylic polymer, wherein the mass of said outer layer coat, calculated on a dry pellet core basis, is within the range of 2.5–15%. The amount of gastro-resistant coating based on acid-resistant acrylic polymers depends on the size of the pellet core to be coated. For example, the smaller the size of the pellets is, the more coating that is needed. Moreover, the smaller the pellet size is, the more difficult it is to maintain uniformity of coating in a production batch. The 0.3 to 0.9 mm pellet core size range of the present invention is advantageous with respect to obtaining the desired release profile, for coating homogeneity, and for filling into a final unit dose (capsule) with desired content homogeneity. For such a pellet core size, it has been determined that the amount of outer layer coat should be within the above recited range. Preferably, the amount of the applied coating composition, calculated on dry basis, is between 8–12% (w/w) of the weight of the dried pellet core.

The "acid-resistant acrylic polymer" is a specific kind of the above acrylic polymer having free carboxyl groups. Such polymers are not soluble in acidic aqueous medium, while they are soluble in neutral or basic aqueous medium. Preferred acid resistant acrylic polymers include the Eudragit L series, such as Eudragit L 30 D-55. This acrylic polymer is available as an aqueous suspension, also comprising a small amount of emulsifiers, and may be directly used for coating in suitable coating equipment. In a particular aspect of the invention, the "acrylic polymer" used for the manufacturing of pellet core is advantageously identical with the "acid-resistant acrylic polymer" of the pellet coating. The outer surface layer can additionally contain other acid resistant polymers such as cellulose acetate phthalate, hydroxypropylmethyl cellulose phthalate etc., as well as other pharmaceutically acceptable excipients. For example, an anti-sticking agent, such as talc, may be added to the coating composition to avoid stickiness of the coated granules during the process. Similarly, a plasticizers such as triethylcitrate can improve the characteristics of the final film coat.

The amount of acid resistant acrylic polymer is preferably within the range of 25–95 mass %, more preferably 30 to 75%, and typically 50 to 75%, calculated on a dry basis of the coating layer. Generally the acrylic polymer is the only acid-resistant polymer in the outer layer coat. The remainder of the outer coat layer is pharmaceutically acceptable excipients and/or other acid-resistant polymer(s) as described above.

The pellet cores of the present invention can be made by various known techniques. The main techniques are, e.g. high shear pelletization, fluid bed pelletization, hot-melt and extrusion-spheronization. Suitable equipment for producing pellet cores for the product of the invention comprise high-shear mixer/granulators, such as equipment sold by the Bohle company under the brand name Vagumator (VMA). The VMA is a single-pot system, which combines blending, wet granulation/pelletization and the subsequent drying of solid products in one piece of equipment. Blending and mixing is facilitated by the presence of high shear mixing equipment (impeller and chopper), whilst the drying process is facilitated by the presence of a microwave, nitrogen drying, vacuum drying and a heatable jacketed process vessel wall. Alternate pelletization techniques, as known in the prior art, are however suitable as well.

A granulation method for making the pellets comprises:
a. granulating a mixture of tamsulosin hydrochloride, microcrystalline cellulose, acrylic polymer, water and optionally auxiliary ingredients to form wet pellet cores,
b. drying said wet pellet cores to a residual amount of water of 2–10%;
c. sieving said dried pellet cores to obtain a fraction within the size range of 0.3–0.9 mm;
d. coating said sieved dried pellet cores with a coating composition that comprises an acid-resistant water soluble acrylic polymer; and
e. drying said coated pellet;

wherein said coating step (d) is sufficient to provide said dried coated pellet with 2.5–15 mass % of said coating composition, calculated on the dry pellet core basis. The auxiliary ingredients, which are pharmaceutically acceptable excipients, are typically a lubricant or plasticizer, but is not limited thereto.

A preferred granulator process includes, mixing tamsulosin hydrochloride with microcrystalline cellulose and an anti-sticking agent to form a powder blend, adding a suspension of acrylic polymer and plasticizer in water to the powder blend mixture, granulating the mixture, drying the obtained granules under control of amount of residual water, and sieving the granules to proper size fractions. The drying process may be performed in the granulator or outside in an appropriate dryer. The control of the residual water content in produced pellets may be made, for example, by taking samples of pellets and annealing them in an oven at 105° C., while measuring the weight loss.

The process of coating may be performed in any suitable equipment such as, directly in the high shear mixer/granulator, in a fluid bed coater, or preferably on a coating pan. The results of the coating procedure may be routinely checked by withdrawing a sample of the pellets and determining the release rate of tamsulosin in simulated gastric fluid as described above. However, if the desired amount of release is not achieved, the coating process of the remaining coated pellets, may be repeated until the desired result is obtained. It is indeed also possible to mix various sub-lots of coated pellets with different release rates to obtain a final lot exhibiting the desired rate. If one sub-lot does not yield the desired pellet size distribution, the negative effects can be made up with other sub-lots.

Once the coated pellets have been produced they may be formulated into individual dosage units for administration of tamsulosin for therapeutic and/or prophylactic purposes such as capsules or sachets. Accordingly, the unit dosage forms containing pellets may contain between 0.01 to 10 mg of tamsulosin hydrochloride per unit, preferably from 0.1 to 1 mg of tamsulosin hydrochloride per unit, even more preferably 0.2, 0.4 or 0.8 mg of tamsulosin hydrochloride per unit. Such a unit dose is normally taken from 1 to 3 times daily, preferably once a day. In practice, the physician will determine the actual dosage and administration regimen, which will be the most suitable for the individual patient.

The suitable unit dosage form may comprise pharmaceutically acceptable capsules of a suitable size (e.g. No. 2 size), for example made from hard gelatin or hydroxypropyl methylcellulose. These coated pellets display an excellent flowability and content uniformity.

Capsules with coated pellets of the present invention comprising a unit dosage amount of tamsulosin may be delivered for immediate use in a suitable package comprising advantageously from 5 to 100 capsules. Such package may comprise a blister pack comprising advantageously 10, 14, 20, 28 or 30 capsules, or a plastic or glass container/bottle containing the same amounts of capsules. Any suitable pharmaceutically acceptable package material may be used in production the package unit.

Coated pellets for oral administration of tamsulosin according to the present invention may be used, for example, in the management of functional treatment of symptomatic benign prostatic hypertrophy or hyperplasia (BPH) or other disorders treatable by tamsulosin (the Disorders). The gastro-resistant coating and extended release of tamsulosin from pellet core assures that therapeutic concentration of tamsulosin in blood is maintained for sufficiently long time, without initial dumping in the stomach.

Accordingly, the present invention further provides a method for treating and/or preventing any one or more disorders which comprises orally administering an effective and/or prophylactic amount to a sufferer in need thereof, of tamsulosin or its pharmaceutically acceptable acid addition salt, particularly tamsulosin hydrochloride, which is formulated into a coated pellet comprising the composition as specified above. Preferably, the pellets of the invention are administered once a day, and more preferably after meal. Administration after food intake is advantageous because of better dispersion of pellets in the environment and minimizing damages of tissues of gastrointestinal tract.

The present invention also provides the use of the tamsulosin pellet comprising the composition as specified above, as well as the use of the above process for making the tamsulosin pellet composition itself, for the manufacture of a medicament for treating and/or preventing any one or more of the Disorders. Also, the coated pellets may be used in medical applications in combination with other agents. The combination may be realized in a form of single combination preparation or by separate administration of drugs containing the above agents.

The invention is further illustrated by the following Examples, but should not be construed as being limited thereto.

EXAMPLE 1

Tamsulosin Hydrochloride 0.4 mg Enteric-resistant Pellets

Formula Used:

| Ingredients | g per batch |
|---|---|
| pellet core: | |
| Tamsulosin.HCl | 2.9 |
| Eudragit L 30 D-55 | 401.1 |
| Triethylcitrate | 12.2 |
| Talc | 120.2 |
| Microcrystalline cellulose | 2000.4 |
| Water (demineralized) | 2000.0 |
| pellet coating (1000 g of pellets) | |
| Eudragit L 30 D-55 (30% dispersion) | 166.48 |
| Triethylcitrate | 5.0 |
| Calcium stearate | 10.0 |
| Water (demineralized) | 106.0 |

Manufacturing Process:

High shear mixer/granulator VMA 10 was used.

Tamsulosin hydrochloride was mixed with talc and microcrystalline cellulose to a homogeneous powder blend A suspension of Eudragit, triethyl citrate and water was prepared in a separate vessel The suspension was added to the powder blend and the mixture was granulated.

The produced granulate was dried by vacuum, nitrogen and microwave until the moisture content of the pellets was 2.7%.

The dried granulate was sieved and fractions between 0.3 and 0.85 mm were collected.

The Pellet Size Distribution:

| particle size (mm) | g | % |
|---|---|---|
| x > 1.0 | 307.0 | 14.3 |
| 0.85 < x < 1.0 | 44.0 | 2.0 |
| 0.6 < x < 0.85 | 767.1 | 35.7 |
| 0.5 < x < 0.6 | 857.4 | 39.9 |
| 0.425 < x < 0.5 | 84.4 | 3.9 |
| 0.3 < x < 0.425 | 67.6 | 3.1 |
| x < 0.3 | 20.0 | 0.9 |
| total batch | 2147.5 | 100.0 |

Pellet Coating Process:

1000 g of the proper sized pellets were returned to the VMA 10. The coating was applied at a rate of ±8 ml/min. The coating was applied in 60 minutes. After drying for 1.5 hours, the batch was discharged and samples were taken for examination.

Pellet Coating Results:

The content of residual water, measured by moisture analyzer, of the coated pellets was 10 2.8 %. Weight gain after coating: 6.5%.

The dissolution profile in simulated gastric fluid: less than 5% in 2 hours.

The dissolution profile in pH 6.8 buffer (SIF): 20% in 30 minutes, 35% in 1 hour, 90% in 5 hours.

EXAMPLE 2

Formula Used:

| Ingredients | total weight (g) | dry weight (%) |
|---|---|---|
| pellet core: | | |
| Tamsulosin.HCl | 20.23 | 20.23 |
| Eudragit L 30 D-55 | 2780.75 | 834.33 |
| Triethylcitrate | 83.44 | 83.44 |
| Talc | 834.23 | 834.23 |
| Microcrystalline cellulose | 14000.00 | 14000.00 |
| Water (demineralized) | 14000.00 | |
| Pellet coating (of 13.8 kg pellets) | | |
| Eudragit L 30 D-55 (30% disp.) | 4600 | 1380 |
| Talc | 552 | 552 |
| Triethylcitrate | 138 | 138 |
| Water | 5066 | |

The solids content of this coating suspension is 20.2% (including the triethylcitrate, this is a liquid but it will not evaporate during coating)

Manufacturing Process:

As in Example 1. High shear mixer/granulator VMA 70 was used.

Results:

Yield in pellets of proper size: 13823 g=84.7%.

The content of residual water of the pellets was 3.4%.

Pellet Size Before Coating:

| particle size (mm) | g | % |
|---|---|---|
| x ≧ 0.85 | 0.9 | 1.1 |
| 0.5 < x < 0.85 | 18.7 | 22.1 |
| 0.425 < x < 0.5 | 45.7 | 54.0 |
| 0.3 < x < 0.425 | 16.8 | 19.9 |
| x < 0.3 | 2.5 | 3.0 |
| total sample | 84.6 | 100.0 |

Pellet Coating:

The pellet coating was performed with a 25 l solid pan. Samples at levels of 8, 9, 10, 11 & 12% coating were taken during production for determination of the dissolution profile in SGF.

Results:

Pellet size distribution after coating:

| particle size (mm) | g | % |
|---|---|---|
| x ≧ 0.85 | 14.7 | 3.0 |
| 0.6 < x < 0.85 | 254.3 | 51.1 |
| 0.5 < x < 0.6 | 117.2 | 23.6 |
| 0.425 < x < 0.5 | 100.0 | 20.1 |
| 0.3 < x < 0.425 | 11.1 | 2.2 |
| x < 0.3 | 0.1 | 0.0 |
| total sample | 497.4 | 100.0 |

Dissolution Results:

The dissolution profiles in SGF, basket, 100 rpm gave the following results: at least 10% of coating should be applied to these pellets to match the required dissolution profile in SGF.

The dissolution profile of the made coated pellets in phosphate buffer (basket method, 100 rpm, pH=6.8): 41% in 30 minutes, 59% in 1 hour, 99% in 300 minutes.

All of the patents, articles, and documents mentioned above are incorporated herein by reference in their entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

I claim:

1. A pharmaceutical dosage form comprising a plurality of pellets, wherein each pellet comprises:
   a. a pellet core having a diameter within the range of 0.3–0.9 mm and comprising a tamsulosin hydrochloride, microcrystalline cellulose, a pharmaceutically acceptable water permeable acrylic polymer and water; and
   b. an outer layer coat surrounding said core which comprises a pharmaceutically acceptable acid-resistant acrylic polymer, wherein the mass of said outer layer coat, calculated on a dry pellet core basis, is within the range of 2.5–15%; and
   wherein the plurality of pellets exhibits a dissolution release profile in simulated gastric fluid using Ph. Eur. basket method at 100 rpm which includes releasing less than 10% of the tamsulosin during the first two hours.

2. The dosage form according to claim 1, wherein said pellet core contains 0.05–5.0% mass of tamsulosin hydrochloride, 50–95% mass of microcrystalline cellulose, 2.5–25% mass of the acrylic polymer, 2–10% mass of water, and 0–25% mass of other pharmaceutically acceptable excipients, calculated on a dry pellet core basis.

3. The dosage form according to claim 1, wherein said pellet core contains 2.5–5% mass of water, calculated on a dry pellet core basis.

4. The dosage form according to any one of claim 1, wherein said water permeable acrylic polymer is an Eudragit L polymer.

5. The dosage form according to claim 1, wherein the composition of said outer layer coat comprises 25–75 mass % of said acid resistant acrylic polymer, calculated on a dry basis.

6. The dosage form according to claim 5, wherein said acid-resistant acrylic polymer is an Eudragit L polymer.

7. The dosage form according to claim 6, wherein the acrylic polymer contained in said pellet core is identical with said acid-resistant acrylic polymer in said outer layer coat.

8. The dosage form according to claim 1, wherein said mass of said outer layer coat, calculated on a dry pellet core basis, is within the range of 8–12%.

9. The dosage form according to claim 1, wherein said coated pharmaceutical pellet exhibits a dissolution release profile in a phosphate buffer of pH 6.8 using Ph. Eur. basket method at 100 rpm which includes releasing 15–45% of the tamsulosin in 30 minutes.

10. The dosage form according to claim 9, wherein dissolution profile includes releasing 30–65% of the tamsulosin in one hour.

11. The dosage form according to claim 10, wherein dissolution profile includes releasing more than 80% of the tamsulosin in five hours.

12. The dosage form according to claim 1, wherein said dosage form is a capsule or sachet.

13. The dosage form according to claim 1, wherein a total amount of tamsulosin hydrochloride contained therein is within the range of 0.1 to 1 mg.

14. The dosage form according to claim 13, wherein said total amount of tamsulosin hydrochloride is 0.2, 0.4, or 0.8 mg.

15. A process, which comprises:
   a. granulating a mixture of tamsulosin hydrochloride, microcrystalline cellulose, acrylic polymer, water and optionally auxiliary ingredients to form wet pellet cores,
   b. drying said wet pellet cores to a residual amount of water of 2–10%;
   c. sieving said dried pellet cores to obtain a fraction within the size range of 0.3–0.9 mm;
   d. coating said sieved dried pellet cores with a coating composition that comprises an acid-resistant water soluble acrylic polymer; and
   e. drying said coated pellet;
wherein said coating step (d) is sufficient to provide said dried coated pellet with 2.5–15 mass % of said coating composition, calculated on the dry pellet core basis.

16. The process of claim 15, wherein said coating step (d) is performed in a high shear mixer/granulator.

17. The process of claim 15, wherein said coating is performed in a fluid bed coater.

18. The process of claim 15, wherein said coating is performed on a coating pan.

19. A process, which comprises:
   (a) granulating a mixture of tamsulosin hydrochloride, microcrystalline cellulose, acrylic polymer, water and optionally auxiliary ingredients to form wet pellet cores,
   (b) drying said wet pellet cores to a residual amount of water of 2–10%; sieving said dried pellet cores to obtain a fraction within the size range of 0.3–0.9 mm;
   (c) coating said sieved dried pellet cores with a coating composition that comprises an acid-resistant water soluble acrylic polymer;
   (d) drying said coated pellet;
   (e) testing a sample of said dried coated pellets for dissolution rate in a simulated gastric fluid; and
   (f) repeating the coating process on the remaining dried coated pellets until a desired amount of release is achieved in said testing step (e).

20. A method for treating the symptoms of benign prostatic hyperplasia, which comprises administering an effective amount of the pellets according to claim 1, to a patient in need thereof.

21. The dosage form according to claim 5, wherein said outer layer coat comprises 30 to 75% of said acid-resistant acrylic polymer.

* * * * *